US00PP25654P3

(12) United States Plant Patent
Olesen

(10) Patent No.: US PP25,654 P3
(45) Date of Patent: Jun. 30, 2015

(54) MINATURE ROSE PLANT NAMED 'POULPAR080'

(50) Latin Name: ***Rosa* hybrid**
Varietal Denomination: Poulpar080

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensbore (DK)

( * ) Notice: Subject to any disclaimer, the term of this patent is extended or adjusted under 35 U.S.C. 154(b) by 39 days.

(21) Appl. No.: 13/986,929

(22) Filed: Jun. 14, 2013

(65) Prior Publication Data

US 2014/0373213 P1 Dec. 18, 2014

(51) Int. Cl.
*A01H 5/00* (2006.01)

(52) U.S. Cl.
USPC ..... Plt./119

(58) Field of Classification Search
USPC ..... Plt./119
See application file for complete search history.

*Primary Examiner* — Anne Grunberg

(57) ABSTRACT

A new miniature rose plant that has abundant, orange flowers and attractive foliage. The variety successfully propagates from softwood cuttings and is suitable for year-round production in commercial glasshouses. This new and distinct variety has shown to be uniform and stable in the resulting generations from asexual propagation.

3 Drawing Sheets

Botanical designation: *Rosa* hybrid.
Variety denomination: 'Poulpar080'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpar080', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant orange flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar080' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar080' was selected by the inventor as a single plant from the progeny of the hybridization in 2007.

Asexual reproduction of 'Poulpar080' by cuttings was first done by Mogens N. Olesen in the nursery in Fredensborg, Denmark in 2008. This initial and other subsequent propagations conducted in controlled environments have demonstrated that the characteristics of 'Poulpar080' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar080'.

Specifically illustrated in FIG. 1 are the flowers whole and in parts.

Figure 1:
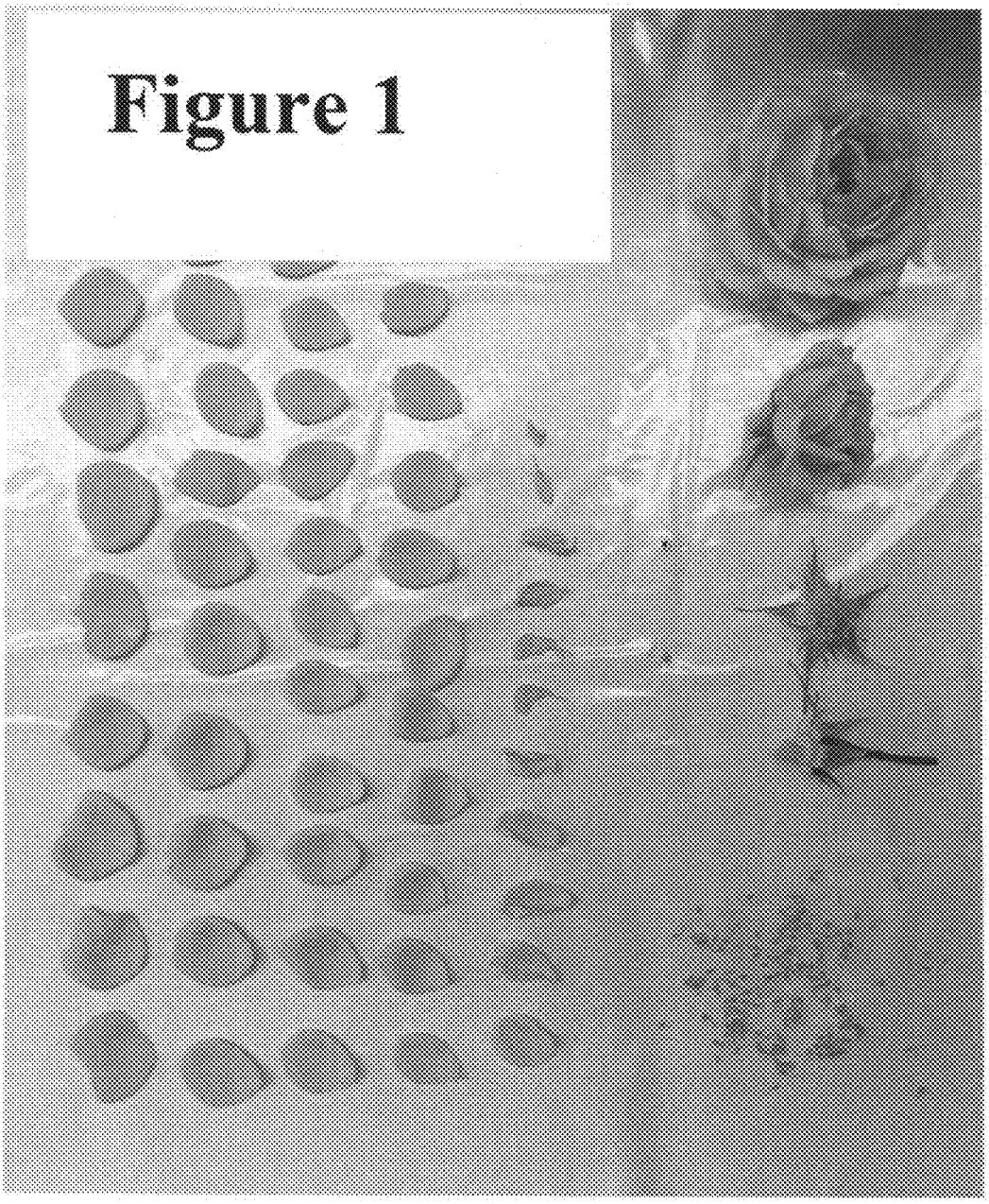
Figure 2:
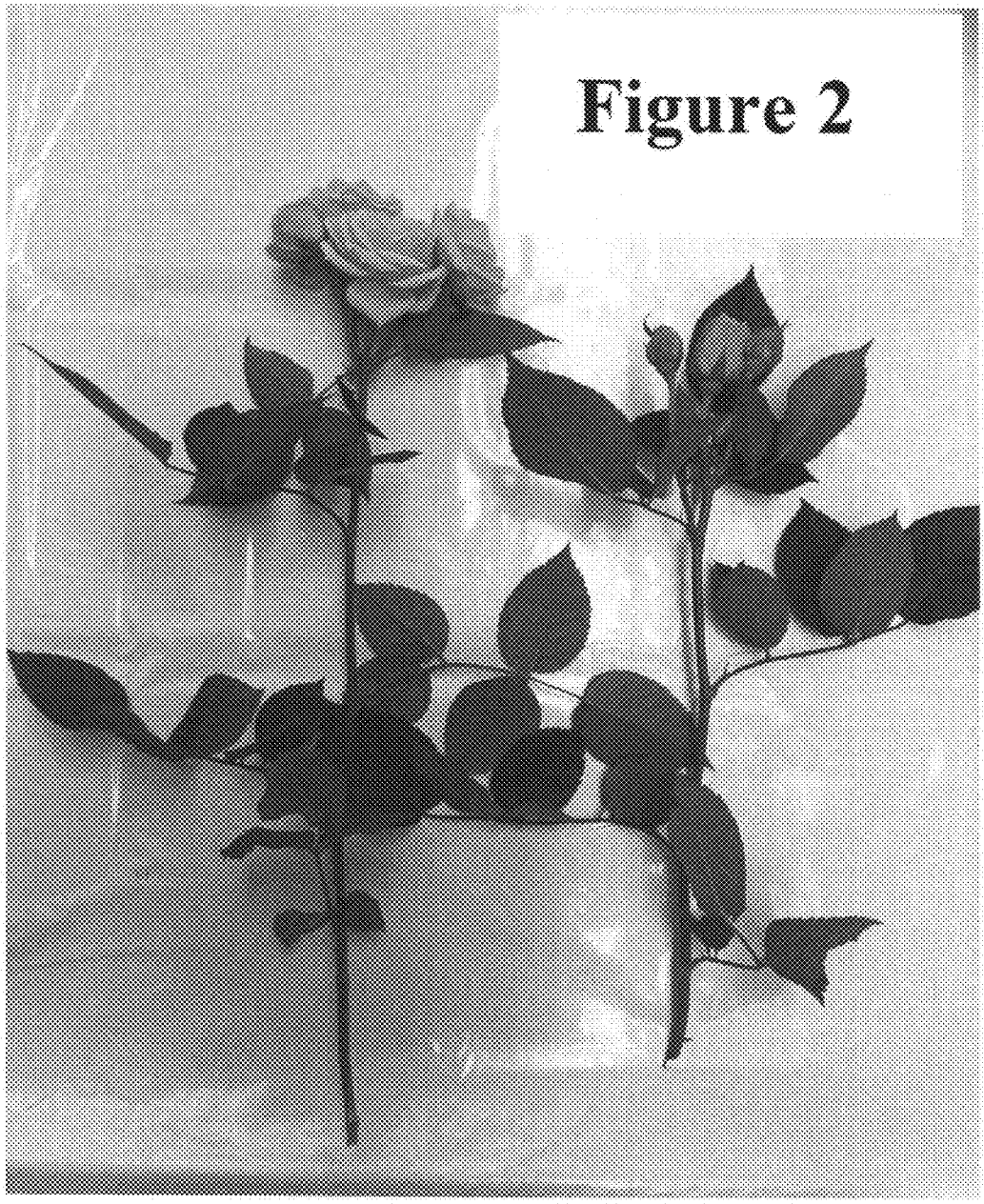

Illustrated in FIG. 2 are flowering stems, showing flower buds, flower clusters, leaves, stems, and attachment of leaves to the stems.

Figure 3:
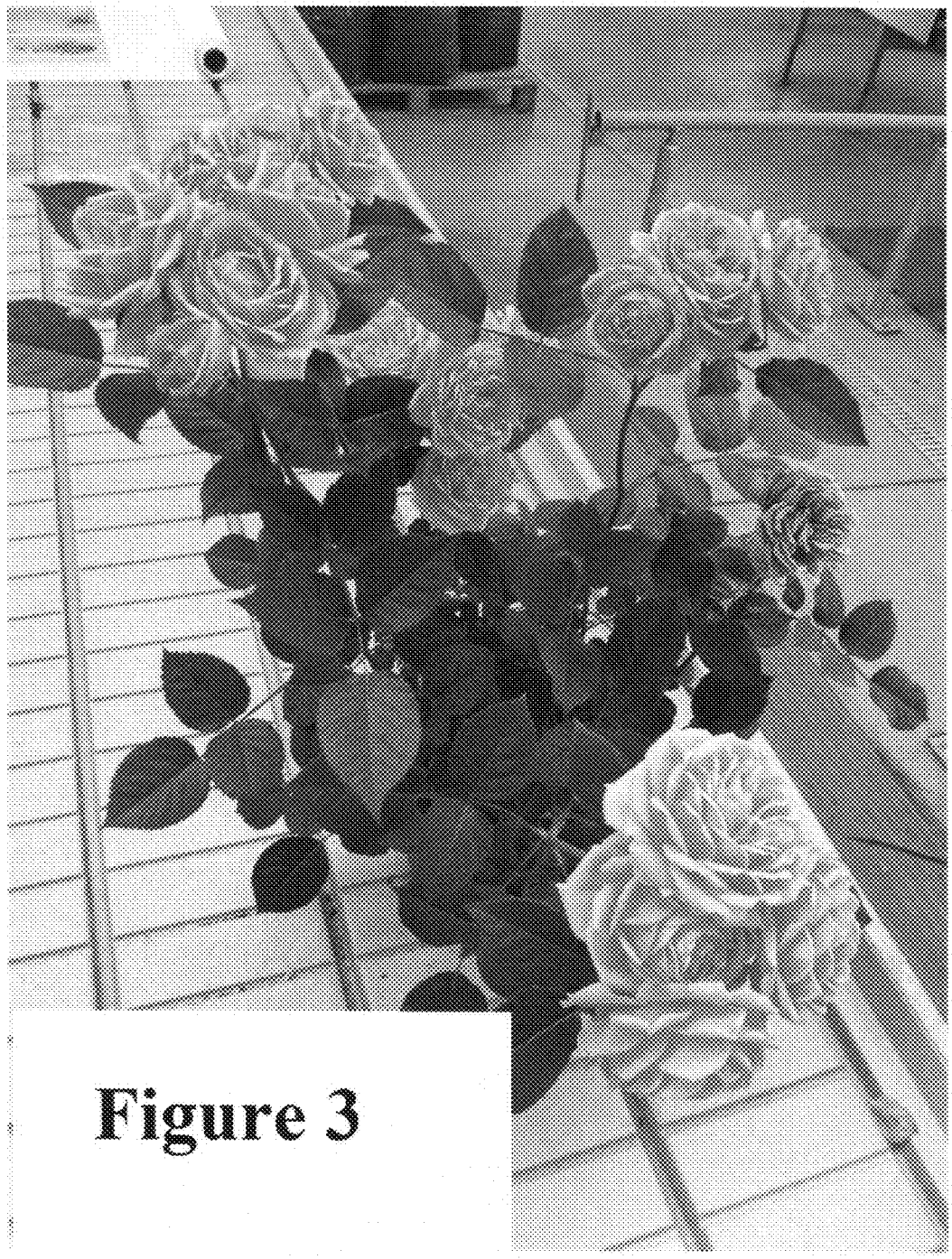

Illustrated in FIG. 3 is the entire flowering plant.

DETAILED DESCRIPTION OF THE VARIETY

The following is a description of 'Poulpar080', as observed in its growth in glasshouses in Fredensborg, Denmark. Observed plants are 12 months of age and were cultivated in 23 cm pots. Color references are made using The Royal Horticultural Society (London, England) Colour Chart, 2001, except where common terms of color are used.

For a comparison, several physical characteristics of the rose variety 'Poultrav', U.S. Plant Pat. No. 13,368 are compared to 'Poulpar080' in Chart 1.

CHART 1

| | 'Poulpar080' | 'Poultrav' |
|---|---|---|
| Petalage: | 52 petals, 7 to 10 of which are petaloids. | 38-44 petals |
| Flower Diameter: | 50 to 70 mm | 40 mm |
| General Tonality of Flower Color: | Yellow-Orange Group 23A | Orange Group 24B |

FLOWER AND FLOWER BUD

Blooming habit: Continuous.

Flower bud:

*Size.*—Upon opening, 30 mm in length from base of receptacle to end of bud. 12 mm in diameter.

*Bud form.*—Ovate.

*Bud color.*—As sepals unfold, petals are Red Group 48A.

*Sepals.*—Upper Surface: Color: Green Group 138B. Texture: Smooth, weakly pubescent. Lower Surface: Color: Yellow Green Group 144A. Texture: Somewhat rough. Shape: Apex: Cirrhose. Base: Flat at union with receptacle. Margins: Margins have weak foliaceous appendages on three of the five sepals. Size: 30 mm long by 7 mm wide.

*Receptacle.*—Surface Texture: Smooth. Shape: Campanulate. Size: 7 mm tall and 10 mm wide. Color: Yellow Green Group 144A.

*Pedicel.*—Surface: Smooth. Length: 30 to 60 mm. Diameter: Generally 3 mm. Color: Yellow-Green Group 144A. Strength: Strong.

*Peduncle.*—Surface: Smooth. Length: 5 to 20 cm. Diameter: 3 to 4 mm. Color: Yellow-Green Group 144A.

*Borne.*—Singly, or in clusters of 3 to 5 resembling a corymb.

Flower bloom:

*Fragrance.*—Light floral scent.

*Duration.*—Flowers last up to 20 days.

*Size.*—Flower diameter is 50 to 70 mm when open. Flower depth is 30 mm.

*Form.*—General shape is a rosette with many slightly overlapping petals.

*Shape of flower, side view.*—The upper portion is flat. The lower portion is flat.

Petalage: Under normal conditions, flowers have 52 petals, 7 to 10 of which are petaloids.

Color:

*General tonality.*—On open flower Yellow-Orange Group 23A.

*Upon opening, petals.*—Outermost petals are Yellow-Orange Group 22A on the upper surface. Orange Group 28B on the lower surface. Innermost petals are Yellow-Orange Group 23B on the upper surface. Red-Orange Group 34C on the lower surface. No distinctive coloration at the base of the petals.

*After opening, petals.*—Outermost petals are Yellow-Orange Group 15B on the upper surface. Orange Group 24B on the lower surface. Innermost petals are Yellow-Orange Group 15B on the upper surface. Orange Group 24B on the lower surface. No distinctive coloration at the base of the petals.

Petals:

*Petal reflex.*—Weak.

*Margin.*—Entire, with weak undulations. Some petals have a point at the center. Some petals have a cleft at the center.

*Shape.*—Generally broad and narrow elliptic. Apex shape: Rounded, cuspidate, and emarginate. Base shape: Rounded and acute.

*Size.*—35 mm (l) by 25 mm (w).

*Texture.*—Smooth.

*Thickness.*—Average.

Petaloids:

*Quantity.*—7 to 10.

*Shape.*—Irregular, and asymmetric. The apex and base are acute.

*Color.*—Yellow-Orange Group 15B on the upper surface. Orange Group 24B on the lower surface.

*Size.*—20 mm (l) by 10 mm (w).

Reproductive organs:

*Pollen.*—None Observed.

*Anthers.*—Size: 2 mm long. Color: Orange Group 24A. Quantity: 160 on average.

*Filaments.*—Color: Yellow-Orange Group 23B. Length: About 6 mm.

*Pistils.*—Length: About 10 mm long. Quantity: 75 on average.

*Stigmas.*—Slightly superior relative to the length of the filaments and the height of the anthers. Color: Yellow Group 10A.

*Styles.*—Color: Yellow Group 10D.

*Seed formation.*—Not observed.

PLANT

Plant growth: Upright. Plants are 45 to 55 cm in height, and 20 to 40 cm wide.

Stems:

*Color.*—Juvenile growth: Yellow-Green Group 144A. Mature growth: Yellow-Green Group 146A.

*Length.*—Canes are 40 cm from the base of the plant to the flowering portion on average.

*Diameter.*—5 to 6 mm.

*Internodes.*—On mature canes 40 to 90 mm between nodes.

*Surface texture.*—Young and mature wood is smooth.

Prickles: None observed.

Plant foliage:

*Compound leaf size.*—130 to 190 mm (l) by 90 to 150 mm (w).

*Quantity.*—2 leaves per 10 cm of stem.

*Color of juvenile foliage.*—Upper Leaf Surface: Green Group 137A. Lower Leaf Surface: Green Group 138B.

*Color of mature foliage.*—Upper Leaf Surface: Green Group 139A. Lower Leaf Surface: Green Group 138B.

Plant leaves and leaflets:

*Stipules.*—Size: About 15 mm in length. Shape: Linear, slightly broad based with outward extending apecies. Margins: Finely serrated with many stipitate glands. Color: Yellow-Green Group 146B.

*Petiole.*—Length: 28 mm on average. Diameter: About 2 mm. Upper surface: Yellow-Green Group 146A with Greyed-Purple anthocyanin. Lower surface: Yellow-Green Group 146B.

*Rachis.*—Length: 22 to 50 mm. Diameter: About 2 mm. Upper surface: Yellow-Green Group 146A with Greyed-Purple anthocyanin. Few stipitate glands. Lower surface: Yellow-Green Group 146B with small prickles.

*Leaflet.*—Number of leaflets: Average 5 on normal leaves in middle of the stem. Size: 65 to 80 mm in length by 50 to 115 mm wide. Margin: Doubly serrate. General Shape: Elliptical. Apex Shape: Mucronate. Base Shape: Round. Texture: Rough. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpar080', substantially as illustrated and described herein, due to its abundant, orange flowers, vigorous growth, compact habit, suitability for production from softwood cuttings in pots, and durable flowers and foliage that make the variety suitable for distribution in the floral industry.

* * * * *